United States Patent [19]
Komine et al.

[11] Patent Number: 5,786,056
[45] Date of Patent: Jul. 28, 1998

[54] LIQUID ABSORBENT MATERIAL USED IN A POUCH FOR A STOMA

[76] Inventors: Keiji Komine, 17-25, Motonakayama 3-chome, Funabashi-shi, Chiba; Ryuzo Ishigaki, B-201, 8-4, Gamou-Atagocho, Koshigaya-shi, Saitama, both of Japan

[21] Appl. No.: 838,804

[22] Filed: Apr. 10, 1997

[51] Int. Cl.⁶ .................................................. B32B 3/30
[52] U.S. Cl. ...................... 428/43; 428/167; 604/365; 604/368; 604/374
[58] Field of Search ........................ 428/43, 167, 905; 604/332, 333, 359, 365, 368, 366, 374

*Primary Examiner*—Alexander Thomas
*Attorney, Agent, or Firm*—IP Group of Pillsbury Madison & Sutro, L.L.P.

[57] ABSTRACT

A liquid absorbent material used in a pouch for a stoma comprising a laminate sheet having surface layers formed of water soluble or dispersible paper and an intermediate layer formed of a web comprising a mixture of a fibrous cellulosic absorbent resin and a powdery synthetic polymeric absorbent resin, wherein a plurality of linear recesses are arranged at such a pitch that the laminate sheet is easily tearable into each of fine sticks that can be inserted, for example, from a urine discharging tube into a stoma pouch for a urinary tract stoma. Liquid excrements flowing out of the stoma into the bag of the pouch can be rapidly solidified into jelly by the liquid absorbent material, thereby reliably preventing liquid excrements or bad smells thereof from leaking through the attaching port of the pouch or the like and preventing liquid excrement from deposition to the adhesives used for securing the pouch to the abdominal wall which would lead to deterioration of tackiness of the adhesives, to enable repeating use of the stoma pouch.

7 Claims, 3 Drawing Sheets

5,786,056

LIQUID ABSORBENT MATERIAL USED IN A POUCH FOR A STOMA

BACKGROUND OF THE INVENTION

FIELD OF THE INVENTION

The present invention concerns a liquid absorbent material to be used in a pouch for a stoma attached to a discharging port of a digestive tract stoma (artificial anus) or urinary tract (artificial bladder).

Stoma pouches include those attached to a discharging ark port of a digestive tract stoma prepared by leading out a cut end of an intestine, from which a lesional part is excised by operation, through an aperture perforated in an abdominal wall and sutured to the abdominal wall and those attached to a discharging port of a urinary tract stoma prepared by perforating an aperture through an abdominal wall for discharging urine sent from a kidney to the outside of a body.

The pouches of these types are adapted to receive feces or urine discharged occasionally and involuntarily from a stoma, which can not control discharge by the own will of a wearer, into a bag such as a vinyl plastic bag for disposal and administration. The bag has an attaching port having a hole as a receptacle of excrements flowing out of the stoma and a flange disposed at the periphery of the hole, and the bag is attached by fixing the attaching port to the abdominal wall and suspending the bag from the abdominal wall.

The method of fixing the attaching port of the pouch to the abdominal wall includes coating adhesives to the flange of the attaching port and appending the flange directly to the skin of the abdominal wall, appending to a face plate fixed previously by adhesives to the skin of the abdominal wall, attaching a packing ring for prevention of liquid leakage to the flange of the attaching port and fitting the packing ring to an annular rib protruded from the face plate.

Further, the pouch for the urinary tract stoma has a urine discharging tube as a drain disposed at the bottom of a bag for flowing out urine. The urine discharging tube is formed with a fine and elongate soft plastic tube having about 5 to 6 mm inner diameter and about 70 to 80 mm length. The pouch also has a drain stopper such as a cap that covers the top end for closing the tract or a clip for collapsing and closing the tubular tract.

The pouch for the digestive tract stoma includes a tightly closed disposable type with no drain which is discarded after the use only for once and a lower open type having a drain aperture perforated at the bottom of the bag for repeating use. The lower open type pouch has a clip stopper for closing the drain aperture.

The drain is disposed to decrease the frequency of exchanging the pouch thereby moderating economical burden or troublesome labor on an ostomate but, actually, the pouch with the drain is not used repeatingly so often.

One of major reasons is that excrements and bad smells thereof are present and remain on the surface of the bag, even after excrements accumulated in the bag are discharged from the drain, and gradually increase bad smells with elapse of time. What is most anxious to the ostomate is leakage of excrements and bad smells thereof from the pouch. Since bad smells of feces are anxious particularly in the pouch for the digestive tract stoma, even the lower open type pouch having the drain aperture were discard so far without repeating use.

The lower open type pouches for the digestive tract stoma, in which a smooth deodorizing film for making feces or bad smells thereof less depositable on the inside of the pouch or in which a powdery or tablet deodorant is incorporated in the bag are also commercially available.

However, even the smooth deodorizing film can not completely discharge feces in the bag through the drain aperture but can provide only such an extent of effect as somewhat decreasing the amount of feces deposited and remained in the bag.

Further, since the deodorant is lost together with discharge of feces through the drain aperture, the deodorizing effect is not long lasting.

Further, the powdery deodorant, if it is incorporated into the pouch as it is, may possibly deposit to the stoma and bring about a worry of causing skin eruption or inflammation to muscosa of the stoma if the deodorant is a chemical substance.

Further, a tablet deodorant, if incorporated into the pouch for urinary tract stoma, may possibly clog the urine discharge tube thus hindering smooth discharge of urine.

Then, another reason of hindering the repeating use of the pouch having the drain is that the water content in the excrements accumulated in the bag of the pouch adheres and penetrates into adhesives used for appending the attaching port to skins or a face plate and deteriorate the tackiness of the adhesives tending to cause peeling of the attaching port and making it impossible to secure the pouch to the abdominal wall.

Particularly, liquid excrements such as diarrhea feces or urine shake or more in the bag of the pouch tending to adhere to and penetrate into the adhesives, and they shake pulsatively during walking or movement to dissolve the adhesives and rapidly lower the tackiness, so that this may cause a worry of dropping the pouch attached to the stoma from a abdominal wall in an early stage.

By the way, excrements accumulated in the bag are disposed by flashing, for example, to a toilet stool through the drain in a case of a pouch with drain and through the attaching port in a case of a pouch with no drain. However, such treatment is extremely troublesome and, if it is done carelessly, diarrhea feces or urine pushed out of the drain or the attaching port are scattered around to possibly contaminate an ostomate's body or garment, or soil the stool or floor surface of the toilet.

Accordingly, it was proposed an invention of disposing a bag of a water soluble paper having a powdery water absorbing resin or a solid block water absorbing resin for gelling watery or soft feces in the bag of a pouch for digestive tract stoma having no drain aperture, to facilitate the disposable of excrements (refer to Japanese Patent Laid-Open Hei 5-175950).

However, the invention has no concerns at all for rapid gelling of excrements regarding the water absorbing resin incorporated in the bag of the pouch, since the invention was proposed perhaps with an aim of facilitating the treatment upon detaching the pouch from the abdominal wall and flashing out the excrements accumulated in the bag through the attaching port.

That is, since the powder of the water absorbing resin sealed in the bag is densely disposed in the bag, it is less disintegratable and takes much time till the entire portion is dissolved in the liquid of the excrements. The solid block water absorbing resin takes a further time. If the resin has a volume and a size corresponding to the volume of the pouch it takes further longer time.

Although the excrements may be entirely gelled till the pouch is detached from the abdominal wall and the excrements accumulated in the bag are disposed, it is impossible, soon after the attaching of the pouch to the stoma, to rapidly gel the liquid excrements flowing out in a great amount from the discharging port of the stoma without shaking them in the bag of the pouch. Accordingly, this prior invention can not overcome the problem that excrements or the bad smells thereof should leak through the attaching port of the pouch attached to the stoma by the shaking of the liquid or excrements adhered to the adhesives used for securing the attaching port of the pouch to the abdominal wall thereby deteriorating the tackiness of the adhesives.

Further, this prior invention relates to a disposable pouch for digestive tract stoma with no drain aperture, so that the pouch can not be used again after the attaching port is once peeled from the abdominal wall and the excrements are discharged through the attaching port thereof since the adhesives bonding the attaching port to the abdominal wall lose the tackiness and have to be discarded. Therefore, this prior invention has no idea of supplementing the water absorbing resin in the bag of the pouch after discharging the excrements.

Further, in the invention described above, a bag having a powder of the water absorbing resin sealed therein or the solid block of water absorbing resin can not but be inserted into the bag through the attaching port of the pouch. However absorbent products exclusively used for this purpose having such a small size that can be inserted as they are through the attaching port have not yet been commercially available.

OBJECT OF THE INVENTION

It is an object of the present invention to provide a liquid absorbent material used exclusively for a pouch which can be supplemented easily by a required amount into a bag of a stoma pouch having a drain with the pouch being secured to the abdominal wall and attached to the stoma for enabling the pouch to be used over and over always in a comfortable condition.

Another object of the present invention is to enable liquid excrements flowing out of the stoma into the bag of the pouch to be gelled rapidly by the liquid absorbent material.

SUMMARY OF THE INVENTION

The foregoing object of the present invention can be attained by a liquid absorbent material to be used in a pouch for a stoma comprising a laminate sheet having surface layers formed of water soluble paper or water dispersible paper and an intermediate layer formed of a web prepared by mixing fibrous cellulosic highly water absorbing resin and a powdery synthetic polymeric highly water absorbing resin and bonding them with water soluble powdery adhesives, wherein a plurality of linear recesses are arranged at a predetermined pitch such that the laminate sheet is torn into each of a stick-shape of a unitary width that can be inserted from a urine discharging tube into a bag of a pouch for a urinary tract stoma.

DETAILED DESCRIPTION OF THE INVENTION

Since the laminate sheet can be inserted as it is also through the attaching port of a pouch for a urinary tract stoma if the sheet is made into such a size that can be inserted through a drain aperture into a bag of a pouch for a digestive tract stoma without tearing but by merely rolling or folding the same. Accordingly, also for the pouch used for a urinary tract stoma, it is not necessary to tear the sheet into each of unitary width pieces that can be inserted through the urine discharge tube upon initial use but it may suffice to tear the sheet into such an appropriate size as capable of obtaining a required amount corresponding to the volume of the pouch.

Further, since the laminate sheet has a plurality of recesses within a surface each at a predetermined pitch of uniformly for enlarging the surface area, if the sheet is used as it is without tearing into pieces, the sheet absorbs liquid over the entire surface uniformly and rapidly.

Moreover, the intermediate layer of the laminate sheet is formed of the web that allows uniform and rapid penetration of a liquid by a capillary phenomenon and the fibrous cellulosic highly water absorbing resin and the powdery synthetic polymeric highly water absorbing resin mixed therewith are dissolved under swelling or swollen under water absorption in water within several seconds to several tens seconds. Accordingly, they are entirely dissolved and swollen uniformly and rapidly by the liquid penetrating into the web.

That is, when the laminate sheet is inserted into the bag of the pouch for digestive tract stoma or the bag of the pouch for urinary tract stoma, the water soluble paper or water dispersible paper constituting the surface layers is rapidly dissolved and dispersed in the liquid of excrements flowing out of the stoma into the bag, and the fibrous cellulosic highly water absorbing resin and the powdery synthetic polymeric highly water absorbing resin mixed therewith constituting the webs of the intermediate layer absorb the water content of the excrements in a not releasable manner dissolve and swell uniformly thereby rapidly gelling the liquid excrements and solidifying them into jelly.

Accordingly, it is possible to prevent that the liquid excrements flowing out of the discharging port of the stoma from shaking in the bag of the pouch thereby leaking the bad smells of the excrements to the outside through the attaching port of the pouch, or to prevent the attaching port from dropping out of the abdominal wall by the adherence of the liquid of the excrements to the adhesives used for securing the attaching port to the abdominal wall.

Since the excrements gelled and solidified into jelly less scatter around upon disposal by discharging them through the drain aperture of the pouch for digestive tract stoma or the urine discharge tube of the pouch for urinary tract stoma, the disposal is facilitated and the amount of the excrements deposited and remained in the bag of the pouch is decreased.

Further, since the laminate sheet entirely dissolves rapidly if used as it is without tearing into pieces, it does not cause a worry of clogging the urine discharge tube of the pouch for urinary tract stoma to hinder the discharge of urine.

Then, after discharging and disposing the excrements from the drain of the pouch, the liquid absorbent material of the present invention is inserted and supplemented in the bag of the pouch through the drain.

Upon insertion, the liquid absorbent material of the present invention can be torn simply into pieces of a desired size with fingers by utilizing recesses formed in the surface of the laminate sheet and, particularly, the sheet can be torn into each stick-shape of unitary width that can be inserted from the urine discharge tube to the bag of the pouch for urinary tract stoma. Accordingly, the absorbent material can be inserted and supplemented easily not only through the drain aperture of the pouch for digestive tract stoma but also through the urinary discharge tube as the drain of the pouch for urinary tract stoma and, in addition, the supplementary amount can be adjusted properly corresponding to the volume of the pouch.

Further, since the intermediate layer of the laminate sheet is formed the web made of the fibrous cellulosic highly water absorbing resin bonded with the water soluble powdery adhesives, even a stick-shape torn piece has a sufficient rigidity to be inserted easily through the urine discharge tube into the bag of the pouch for urinary tract stoma.

Further, the laminate sheet finely torn into stick-shape pieces causes remarkably rapid absorption and penetration of liquid, the sheet is dissolved and dispersed at a high speed in the liquid and is distributed throughout the inside of the bag when it is inserted by a required amount corresponding to the volume of the pouch for urinary tract stoma. Therefore, even urine with no substantial viscosity but flowing easily is completely absorbed to the laminate sheet instantly as it flows out of the urinary tract stoma and is gelled rapidly before it shakes in the bag of the pouch. Thus, there is no worry at all that urine leaks from the attaching port of the pouch or deposits to the adhesives coated on the attaching port thereby deteriorating the tackiness of the adhesives.

Further, while the powder of the synthetic polymeric highly absorbing resin used for the liquid absorbent material in the present invention sometimes has a spiny surface on the particle and when the powder is inserted as it is in the pouch, it may possibly cause pinholes in the bag or deposition of powder to muscosa of the stoma, resulting in skin eruption or inflammation. However, such a worry can be eliminated by disposing the resin powder in the intermediate layer of the laminate sheet as described above.

DESCRIPTION OF PREFERRED EMBODIMENTS

Figure 1:
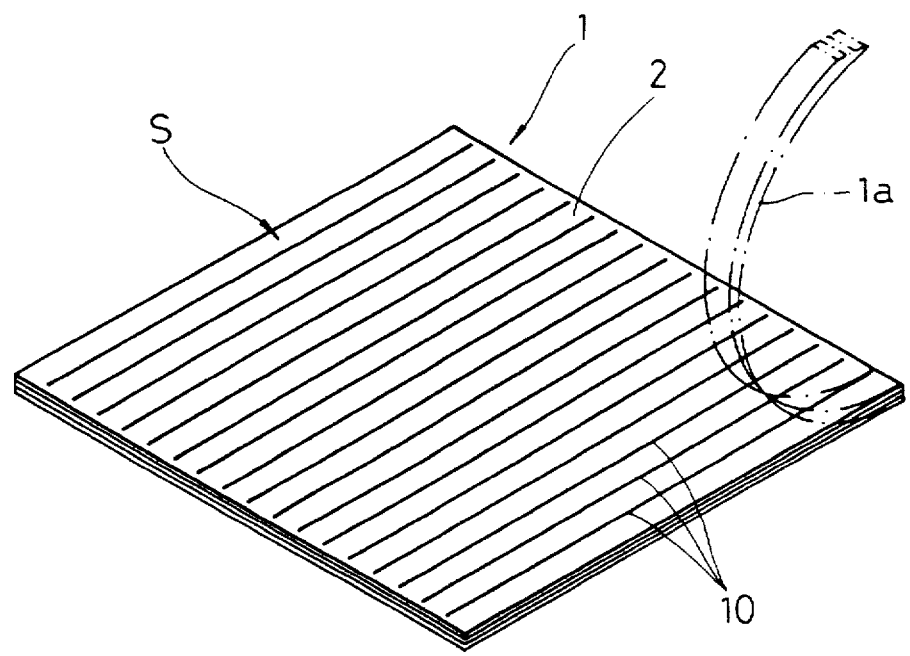
FIG. 1 is a view illustrating a liquid absorbent material of a first embodiment according to the present invention.
Figure 2:
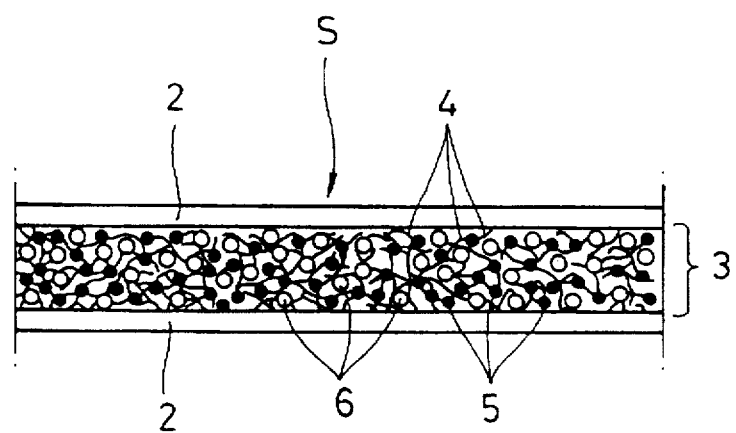
FIG. 2 is a view illustrating a cross sectional structure of the liquid absorbent material.
Figure 3:
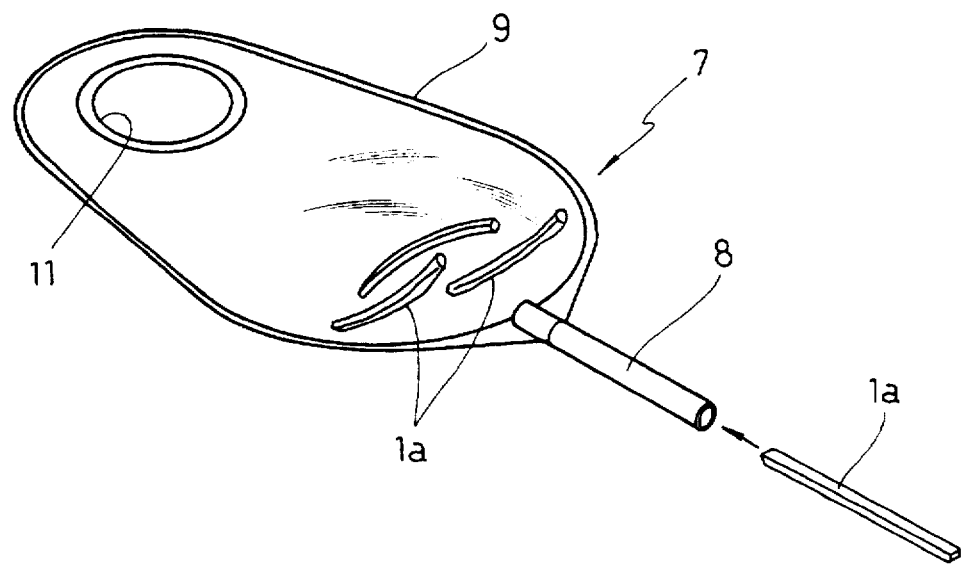
FIG. 3 is a view illustrating the state of using the liquid absorbent material.

A liquid absorbent material 1 used in a pouch for a stoma shown in FIG. 1 and FIG. 2 comprises surface layers 2 and 2 from of soft water soluble paper or water dispersible paper that is dispersed and dissolved in a short period of time of about 5 to 20 sec in water and an intermediate layer 3 formed of a web comprising a mixture of a fibrous cellulosic highly water absorbing resin 4 and a powdery synthetic polymeric highly water adsorbing resin 5 bonded with water soluble powdery adhesives 6 and they are formed into a laminate sheet S having 100 mm length×100 mm width×1.5 mm thickness. Within the surface of the laminate, are formed a plurality of linear recesses 10 each having about 99 to 98 mm length, at a pitch of about 3.5 mm in parallel with each other, such that the laminate sheet S can be torn into each of stick-shape pieces of a unitary width that can be inserted through a urine discharge tube 8 of a pouch 7 for a urinary tract stoma shown in FIG. 3.

Namely, when the laminate sheet having the size of 100 mm length×100 mm width×1.5-3 mm thickness as described above is torn along every recesses 10 disposed at a pitch of about 3.5 mm, a stick-shape liquid absorbent material 1a of 100 mm length and having a cross sectional size of 1.5–3 mm×3.5 mm with a diagonal length of less than 5 mm can be obtained. The stick-shape liquid absorbent 1a can be inserted easily into the bag 9 through the urine discharge tube 8 of about 5–6 mm inner diameter disposed to the pouch 7 for urinary tract stoma commercially available at present.

Further, by properly adjusting the number of the stick-shape liquid absorbent materials 1a to be inserted, an appropriate amount of the liquid absorbent material can be supplemented corresponding to the volume of the bag 9 of the pouch 7 for urinary tract stoma.

Alternatively, the sheet sized about 100 mmL×100 mmW×1.5–3 mmH can be inserted being rolled as it is into the bag 9 through the attaching port 11 of the stoma pouch 7, or can be inserted as it is also through the attaching port or the drain aperture of the pouch for digestive tract stoma. It is also possible to supplement the liquid absorbent material by tearing the laminate sheet for several pitches of recesses 10 into a rectangular shape by an amount corresponding to the volume of the pouch.

The surface layers 2 and 2 of the laminate sheet S is made of water soluble paper consisting of carboxymethyl cellulose material or thin water dispersible paper of about 13 g/m$^2$ weight.

In the intermediate layer 3 of the laminate sheet S, fibrous carboxymethyl cellulose of 0.8 to 1.5 mm fiber length formed by carboxymethylating natural cellulose fibers is used for the fibrous cellulosic highly water absorbing resin 4, and a polyacrylate highly water absorbing resin that provides gelled excrements with smooth and dry feeling is used for the powdery synthetic polymeric highly water absorbing resin 5. Polyolefinic powdery adhesives showing thermal adhesion at 131° C. are used for the water soluble powdery adhesives 10. The intermediate layer 3 is formed by mixing the components while uniformly dispersing them in an air stream, accumulating spontaneously by gravitational falling to a predetermined thickness, and then pressing and heating them to form a bonded web, in which fibers of the cellulosic highly water absorbing resin 4 are stacked and bonded. Liquid of the excrements rapidly penetrates throughout the intermediate layer 3 by the capillary phenomenon caused between each of the fibers of the web.

Thus, the liquid of the excrements prevails throughout the fibrous cellulosic highly water absorbing resin 4 forming the web of the intermediate layer 3, or the powdery synthetic polymeric highly water absorbing resin 5 mixed therewith and fixed being distributed between the fibers of the web, by which the highly water absorbing resin is uniformly dissolved and swollen and the liquid excrements are rapidly gelled.

A web prepared, for example, by blending the fibrous carboxymethyl cellulose and the polyolefin powdery adhesives at 98:2–60:40 by weight ratio and mixing a powdery polyacrylate type highly water absorbing resin by an amount corresponding to 200–400% by weight of the fibrous carboxymethyl cellulose has a water absorption of not less than 9000 g/m$^2$, and the web can rapidly and reliably suppress the shaking of liquid excrements flowing out into the bag of the stoma pouch.

Particularly, since the fibrous carboxymethyl cellulose has a nature of dissolving rapidly and causing separation between the fibers when immersed in water with no mechanical stirring to form an aqueous solution, it rapidly dissolves upon only contact with the liquid excrements stored in the bag of the pouch.

Further, if a powdery deodorant is mixed in the web of the intermediate layer, to which the liquid of the excrements penetrate uniformly and rapidly, the deodorant dissolves at a high speed and shows high deodorizing effect. As the powdery deodorant, use of green tea extracts prepared by extracting leaves of Japanese tea into hot water, purified with ethanol and then drying into a powdery form (green tea extracts MF manufactured by Maruzen Seiyaku Co.) is particularly suitable as the deodorant for the stoma pouch since the extracts are harmless to human bodies, cause no worry of skin eruption or inflammation to the ostomate's muscosa if they should be adhered thereto and since the green tea extracts have an effect of deodorizing ammonia of lowering the ammonia residue to 3% by merely adding 1% extracts to a liquid containing 75 ppm of ammonia.

The powdery deodorant comprising the green tea extracts may be mixed in water, coated on the surface of the laminate sheet S, dried and then adhered on the surface layers 2 and 2.

The liquid absorbent material 1 shown in FIG. 1 is harmless causing no troubles even upon direct contact with skins or injuries, and has a total size corresponding to that of usual styptic gauzes and a remarkably high liquid absorbing performance compared with such styptic gauzes. In addition, the surface area of the absorbent is increased and the air permeability is enhanced and can be torn simply into a required size for use by the provision of a plurality of recesses 10. Accordingly, a great demand can be expected also as styptic articles for surgery operation.

However, if the liquid absorbent material 1 is used being put on a protruded portion of a body, the surface of the laminate sheet S may sometimes be disintegrated along each of the recesses 10 to form a large gap at the recess.

Figure 4:
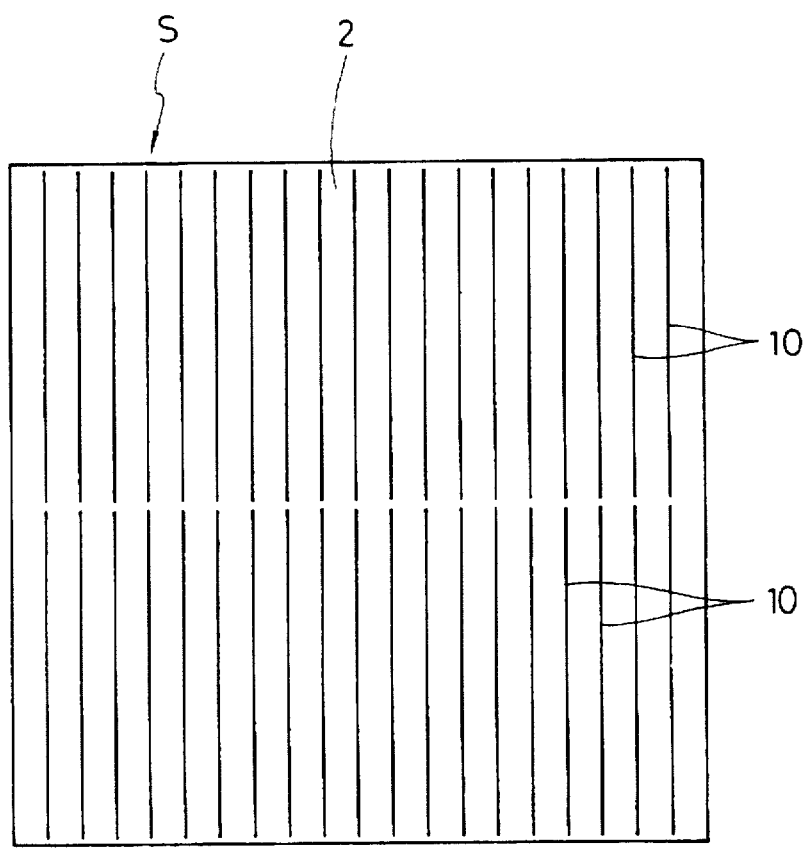
FIG. 4 is a view illustrating a liquid absorbent material of a second embodiment according to the present invention.

A liquid absorbent material shown in FIG. 4 overcomes such a problem. The laminate sheet S has the same laminate structure as that of the liquid absorbent material 1 in FIG. 1, excepting that each of the recesses 10 disposed in parallel with each other at a predetermined pitch is formed as a broken line having one or more intermediate discontinuous portions so as to restrict disintegration in the surface.

Further, the liquid absorbent material of the present invention may be formed into a stick-shape unitary product by previously cutting the laminate sheet S to such a width as can be inserted from the urine discharging tube 8 into the bag 9 of the pouch 7 for urinary tract stoma.

Alternatively, when the laminate sheet S is shaped to a large thickness such that the intermediate layer 3 has a thickness of about 4 to 6 mm and punched to about 3.5 mm width under compression to about 1.5 to 3 mm thickness by a punching die used for punching fabrication, a stick-shape liquid absorbent material cut into such a width as can be inserted into the urine discharging tube 8 of the pouch 7 for urinary tract stoma can be obtained. Since the density of the inter-mediate layer 3 is increased by compression, the liquid absorbent material have a remarkably increased liquid absorption amount per unit area and also have an increased hardness to improve the rigidity and can be inserted easily into the urine discharge tube 10 of the pouch 9 for urinary tract stoma.

Figure 5:
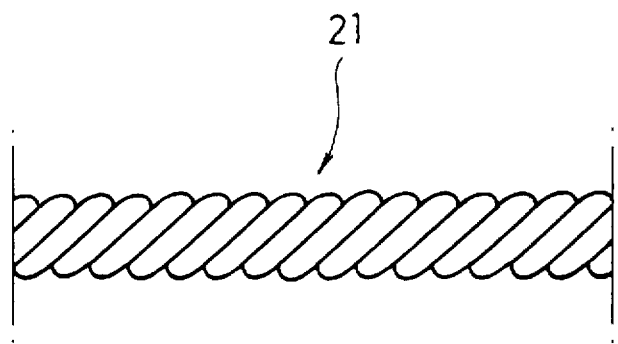
FIG. 5 is a view illustrating a liquid absorbent material of a third embodiment according to the present invention.

Then, as shown in FIG. 5, the laminate sheet S may be formed also as a liquid absorbent material 21 formed into a twisted paper string of a unitary product having such a diameter as can be inserted from the urine discharging tube 8 into the bag 9 of the pouch 7 for urinary tract stoma, by cutting the sheet into plurality of fine strands which are set, for example, by water soluble adhesives to keep the twist.

Since the liquid absorbent material 21 in the form of the twisted paper string has a strong rigidity by the twisting, it can be inserted easily into the urine discharging tube 8 and has a large liquid absorption area.

Further, when the laminate sheet S is cut into a plurality of fine strands by punching and then twisting them, the liquid absorption amount can also be increased remarkably.

What is claimed is:

1. A liquid absorbent material used in a pouch for a stoma comprising a laminate sheet having surface layers formed of water soluble paper or water dispersible paper and an intermediate layer formed of a web prepared by mixing fibrous cellulosic highly water absorbing resin and a powdery synthetic polymeric highly water absorbing resin and bonding them with water soluble powdery adhesives, wherein a plurality of linear recesses are arranged at a predetermined pitch such that the laminate sheet is torn into each of a stick-shape of a unitary width that can be inserted from a urine discharging tube into a bag of a pouch for a urinary tract stoma.

2. A liquid absorbent material used in a pouch for a stoma as defined in claim 1, wherein each of the recesses comprises a recess in the form of a broken line having an intermediate discontinuous portion.

3. A liquid absorbent material used to a pouch as defined in claim 1, wherein a powdery deodorant is mixed in the intermediate layer.

4. A liquid absorbent material used in a pouch as defined in claim 1, wherein a powdery deodorant is coated in the surface layer.

5. A liquid absorbent material used in a pouch for a stoma comprising a laminate sheet having surface layers formed of water soluble paper or water dispersible paper and an intermediate layer formed of a web prepared by mixing fibrous cellulosic highly water absorbing resin and a powdery synthetic polymeric highly water absorbing resin and bonding them with water soluble powdery adhesives, wherein the laminate sheet is cut into such a width as can be inserted from a urine discharging tube into a bag of a pouch for urinary tract stoma, and formed into a stick-shapes unitary product.

6. A liquid absorbent material used in a pouch as defined in claim 5, wherein the laminate sheet is cut by punching.

7. A liquid absorbent material used in a pouch for a stoma comprising a laminate sheet having surface layers formed of water soluble paper or water dispersible paper and an intermediate layer formed of a web prepared by mixing fibrous cellulosic highly water absorbing resin and a powdery synthetic polymeric highly water absorbing resin and bonding them with water soluble powdery adhesives, wherein the laminate sheet is cut into a plurality of fine strands, which are twisted to each other and formed into a twisted paper string shape of a unitary product having such a diameter as can be inserted from a urine discharging tube into a bag of a pouch for urinary tract stoma.

* * * * *